United States Patent
Ross

(10) Patent No.: US 6,196,839 B1
(45) Date of Patent: Mar. 6, 2001

(54) CONTINUOUS USE ORTHODONTIC COOLING APPLIANCE

(76) Inventor: Robert Gregg Ross, 4409 Three Oaks, Arlington, TX (US) 76016

(*) Notice: Subject to any disclaimer, the term of this patent is extended or adjusted under 35 U.S.C. 154(b) by 0 days.

(21) Appl. No.: 09/240,779

(22) Filed: Jan. 29, 1999

(51) Int. Cl.[7] ......................................... A61C 3/00
(52) U.S. Cl. .................... 433/3; 433/32; 62/3.2; 606/20
(58) Field of Search ................ 433/3, 32; 62/3.2, 62/3.3; 606/20, 21, 23

(56) References Cited

U.S. PATENT DOCUMENTS

| | | |
|---|---|---|
| Re. 26,276 * | 10/1967 | Hirschhorn . |
| 3,274,995 * | 9/1966 | Eidus . |
| 3,575,176 | 4/1971 | Crump et al. ............... 128/303.1 |
| 3,618,590 * | 11/1971 | Yardley et al. . |
| 3,782,366 * | 1/1974 | Brown . |
| 3,993,075 | 11/1976 | Lisenbee et al. ............ 128/303.1 |
| 4,207,897 * | 6/1980 | Lloyd et al. . |
| 4,308,012 | 12/1981 | Tamler et al. ..................... 433/32 |
| 4,308,013 * | 12/1981 | Major ............................... 433/32 |
| 4,350,488 * | 9/1982 | Davis ................................ 433/32 |
| 4,440,167 * | 4/1984 | Takehisa ........................... 606/20 |
| 4,519,389 * | 5/1985 | Gudkin et al. .................... 606/20 |
| 4,907,965 * | 3/1990 | Martin ................................. 433/3 |
| 4,993,946 * | 2/1991 | Kirsch .............................. 433/32 |
| 5,035,612 * | 7/1991 | Martin et al. ...................... 433/3 |
| 5,044,947 | 9/1991 | Sachdeva et al. ............... 433/20 |
| 5,207,674 * | 5/1993 | Hamilton .......................... 606/20 |
| 5,816,800 | 10/1998 | Brehm et al. ...................... 433/7 |

* cited by examiner

Primary Examiner—Ralph A. Lewis
(74) Attorney, Agent, or Firm—Charles D. Gunter, Jr.

(57) ABSTRACT

The present invention is a thermoelectric device and method designed to create a martensitic state in a shape memory alloy. The invention allows for prolonged use without overheating, and is more less expensive and easier to use than current art. The device is comprised of a cooling tip that is made of a thermally conductive material in contact with the thermoelectric module powered by an external DC converter. A heat sink is in thermal contact with the heating face of the module with cooling fins to draw heat away from the module. A continuous supply of cooling gas or liquid flows over the cooling fins or liquid channels to further cool the module. The DC power supply is controlled by a pneumatic device that will only operate under positive gas pressure, thus ensuring proper cooling of the heat sink of the invention. The cooling tip extends from the front end of an insulating body, the body having a threaded chucking hold for easy removal and changeout of the cooling tip.

24 Claims, 6 Drawing Sheets

CONTINUOUS USE ORTHODONTIC COOLING APPLIANCE

BACKGROUND OF THE INVENTION

1. Field of the Invention

The present invention relates in general to a thermoelectric device for creating a martensitic state in shape memory alloy, and in particular to a hand held device to be used in orthodontic procedures. Still more particularly, the present invention relates to a thermoelectric cooling device that is continuously gas or liquid cooled to allow continuous use at a constant cooling temperature in orthodontic procedures.

2. Description of the Prior Art

Shape memory alloys have a variety of practical uses, one of which is in orthodontic and other medical procedures. One example of the use of shape memory alloy is the Sachdeva et al. (U.S. Pat. No. 5,044,947)invention of an Orthodontic Archwire and Method of Moving Teeth. In that invention, a nickel-titanium-copper alloy is formed into an arch-shaped wire that holds its shape. The room temperature, rigid state of this alloy is called its austenitic state. However, when a localized portion of the wire is cooled, the metal is placed in a martensitic state. The actual temperature required to bring the wire to its martensitic state may range from about 15° C. to 0 ° C., depending upon the type of wire used. In the martensitic state, the wire becomes soft and pliable in the cooled region. This characteristic is useful in applying the archwire to brackets placed on teeth. Cooling the wire allows easy placement of the wire on a maloccluded tooth, and upon warming to room or body temperature, the archwire tends to go back into its arch-shape, thus correcting the malocclusion.

The problem with using shape memory alloys such as that described in Sachdeva et al. is in conveniently bringing a localized portion of the wire to its martensitic state. Some of the devices and methods in current use by orthodontic practitioners is the use of frozen cotton swabs, placing the wire in a freezer or cooler, or the use of a freezing instrument, an example of which goes by the trade name of POLAR BEARTM™ (Orec Corporation). The latter device is a hollow pencil-shaped device that is filled with water, then frozen. There are several problems with these devices. Once removed from the freezer, the devices must be used immediately. Further, the practitioner must have a freezer close to the patient for cooling the devices. Also, the cotton swab(s) or POLAR BEAR™ do not stay cold enough for a substantial amount of time to be useful for procedures longer than 1–2 minutes without further, time consuming freezing in a freezer.

There are several medical instruments that are hand held cooling devices incorporating a narrow tip for applying to the desired location to be cooled. The Crump et al. (U.S. Pat. No. 3,575,176) invention is a cryosurgical instrument that has a cooling tip, the tip cooled by a refrigerant such as dichlorodifluoromethane or carbon dioxide charged into the device. The device is used mostly in cataract surgery, being used to adhere the cooling tip (which is at −10 to −20° C.) to the tissue to be extracted or handled. The Lisenbee et al. (U.S. Pat. No. 3,993,075) invention is similar to the Crump et al. invention, with the added feature of having a rapid defrosting means. These devices are cumbersome, difficult to use, and use undesirable chemical compounds that escape into the air. Further, they tend to cool the region more than is needed for placing a shape memory alloy in its martensitic state, and may even injure sensitive gum and oral tissues.

Thermoelectric technology, a common technology incorporating the Peltier Effect, would be ideal for use in various medical and orthodontic practices. Thermoelectric devices can be miniaturized to fit into small, hand held instruments, and require little to no maintenance when proper cooling means are provided. There is one hand held device that incorporates thermoelectric technology used for testing the sensitivity of a patient's tooth in order to determine if the tooth is alive or dead, the Tamler et al. (U.S. Pat. No. 4,308,012) invention. This device has a cooling tip that is used to contact the patient's tooth, applying either heat or cold to the tooth, the practitioner then looking for a response from the patient to determine the sensitivity of the tooth. The device has precise and complex electronic circuitry to allow control of the cooling tip temperature and provides an automatic cut-off if the apparatus overheats.

There are several problems with the Tamler et al. device. The first and most inhibiting problem is that it can overheat after prolonged (greater than 1–2 minutes) use, causing the device to automatically cut-off. This makes the device impractical to use in orthodontic procedures, which can last 1–2 hours. Also, the precise circuitry involved increases the cost and maintenance of the device. Finally, the Tamler et al. device does not allow for easy changing out of the cooling tip, which would be useful for various applications as well as for hygienic purposes. Thus, there is a need for a device that is less expensive, easy to use and maintain, and can be used continuously for at least 1 hour. The present invention solves these problems.

SUMMARY OF THE INVENTION

It is therefore on object of the present invention to provide a simple, durable device for creating a martensitic state in a shape memory alloy.

It is another object of the present invention to provide a hand held device for use in cooling a localized portion of an orthodontic archwire made of shape memory alloy.

It is yet another object of the present invention to provide a device that incorporates thermoelectric technology to cool a thermally conductive cooling tip for orthodontic or medical applications.

It is yet another object of the present invention to provide a simple means of allowing rapid change out of the cooling tip for use in different patients and for different applications.

It is yet another object of the present invention to provide a thermoelectric device that can be used for prolonged periods of time without overheating and while maintaining a constant temperature.

It is yet another object of the present invention to provide a cost effective means of placing shape memory alloy in its martensitic state.

The foregoing objects are achieved by providing a device for the continuous cooling of localized portions of a shape memory alloy. The device is comprised of a cooling tip that is made of a thermally conductive material which conducts heat away from its working end towards the cooling face of a thermoelectric module. The cooling tip extends from a hand held instrument that contains the thermoelectric module. The module has a cooling face and a heating face, the cooling face being in thermal contact with a cold sink. The cold sink has a built in chuck for receiving the cooling tip. The cooling tip can be easily replaced and changed out with a clean and/or differently shaped cooling tip.

The heating face of the module is in thermal contact with a heat sink which consists of a distal flat face which contacts the heating face of the module, and a series of parallel cooling fins that extend perpendicular from the plane of the flat face of the heat sink. The design of the heat sink allows rapid and efficient cooling of the heating face of the module, which is vital for allowing continuous use of the device. The cooling tip, cold sink, thermoelectric module, and heat sink form a series of components that are respectively and thermally linked through physical contact. Due to the presence of microscopic crevices and imperfections on the surfaces, it is also desirable to place a thermally conductive substance such as a grease or epoxy between the contacting surfaces. The faces can also be soldered to improve thermal conductivity. The thermal sinks and module are held together mechanically through pressure applied by a spring against the inside surface of an insulating shroud and chucking hold.

A means for allowing a pressurized stream of cooling gas is provided. The gas should be a non-explosive gas such as nitrogen, air, or other inert and non-oxidizing gas. The stream of air is blown against the heat sink by an air tube entering the back end of the hand held instrument. A means for allowing a cooling liquid such as water can also be used to draw heat away from the heat sink. Either method, gas or liquid, provides further cooling of the heating face of the module, thus improving the performance of the device. There is space around the tube and the back end of the shroud to allow the heated air to pass out of the instrument for a continuous flow cooling air. This keeps the instrument from overheating and allows for prolonged use.

Also provided is a power unit that converts AC voltage to a DC voltage, the DC voltage being used to power the thermoelectric module. A pneumatic electric switch is provided in the power unit that allows the device to operate only when there is a positive air pressure applied through the system. This helps prevent overheating of the thermoelectric module and enhances its practical use in a working environment.

Additional objects, features and advantages will be apparent in the written description which follows.

DETAILED DESCRIPTION OF THE INVENTION

Figure 1:
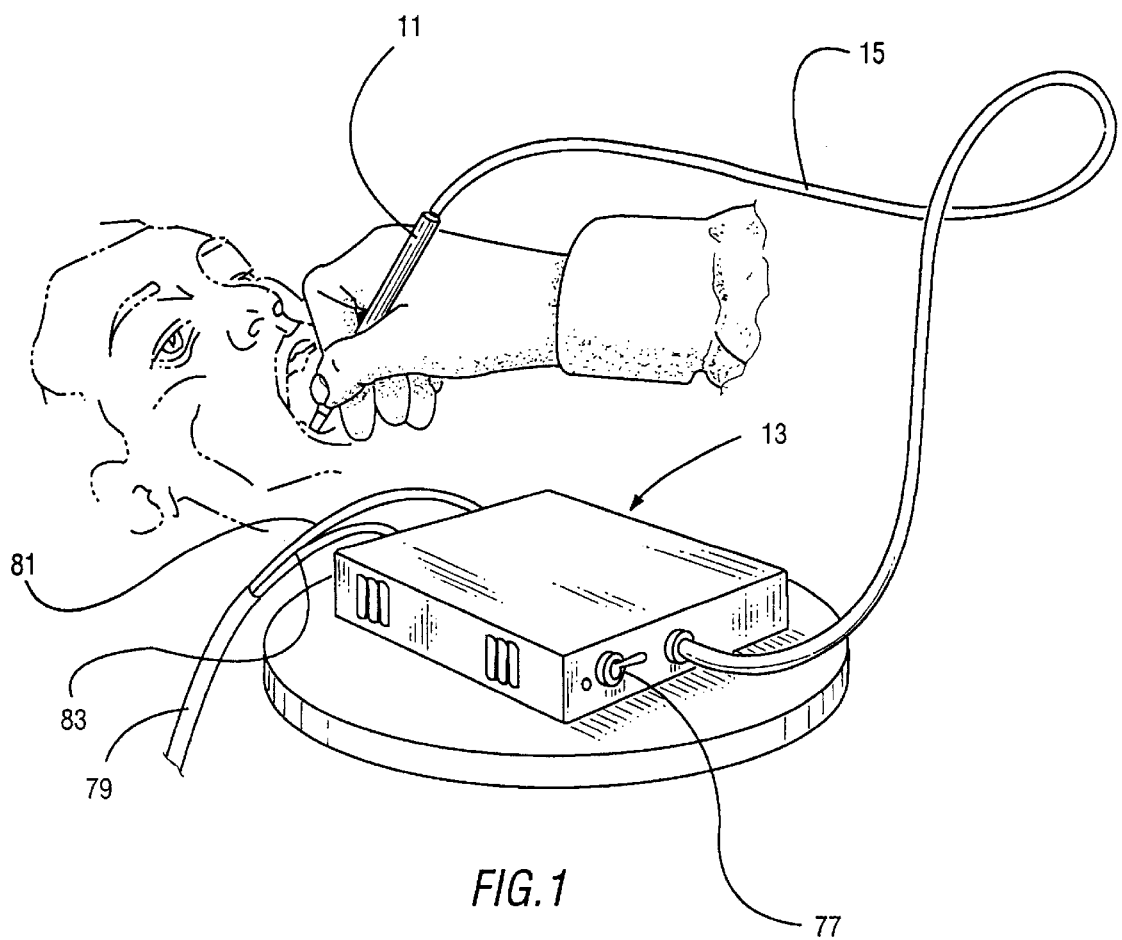
FIG. 1 is a perspective view of the hand held body being used on an archwire of a patient, and the power supply of the invention.

DESCRIPTION OF DEVICE. FIG. 1 shows a perspective view of the present invention. The hand held body 11 of the invention houses elements to be described in more detail below in FIGS. 2–3. Power unit 13 of the invention houses the AC converting unit and pneumatic switch system for controlling power and gas flow to the body. The power unit will be described in more detail in FIG. 4. Compressed gas or cooling liquid is provided through tube 83, while AC voltage is provided through lead 81, the lead and wire being contained in flexible tube 79.

Figure 2:
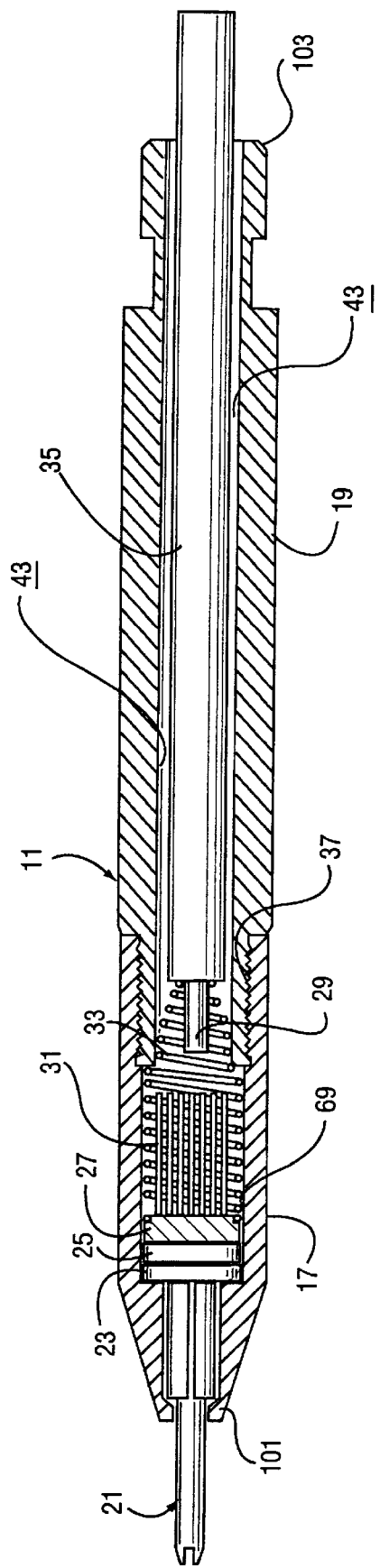
FIG. 2 is a side, cutaway view of the hand held body of FIG. 1 and its internal components.
Figure 4:
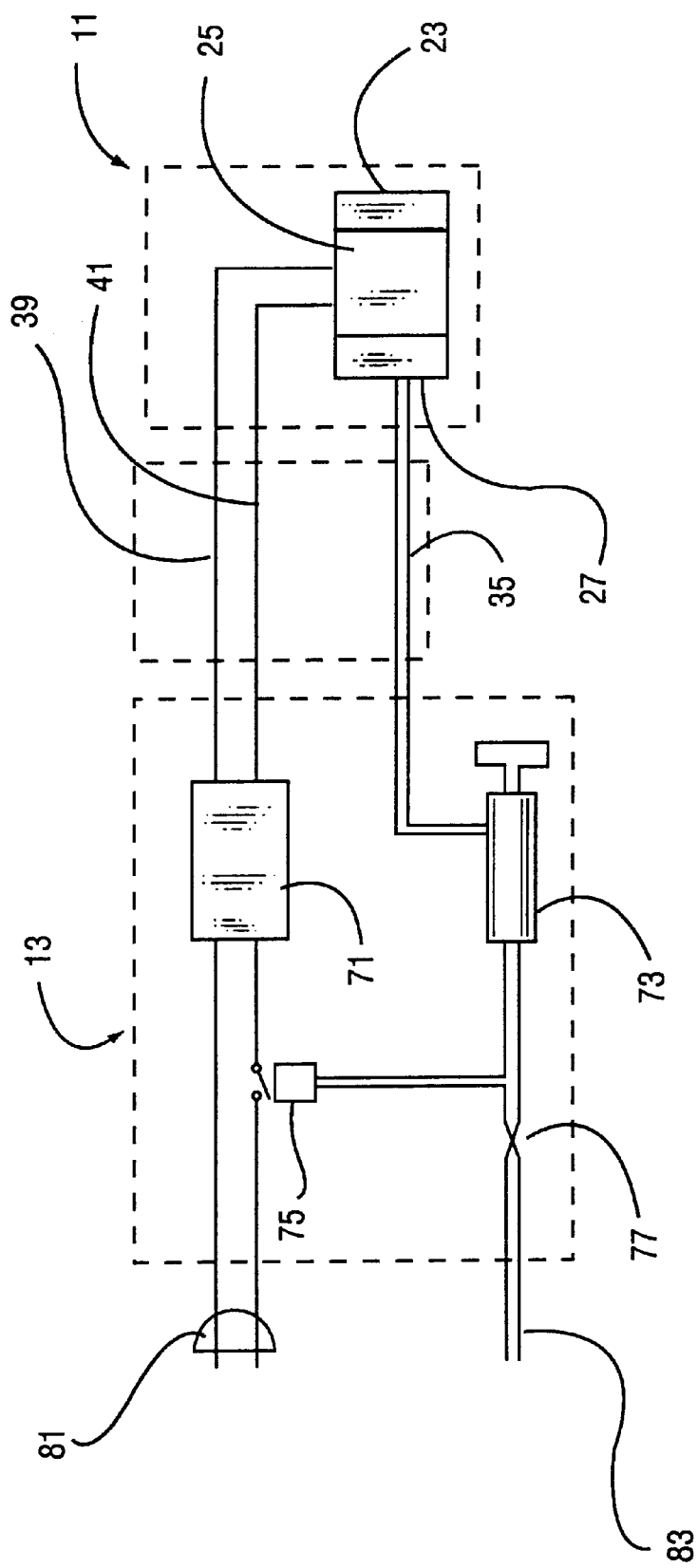
FIG. 4 is a schematic of the electrical circuitry and cooling gas pathway of the invention.

FIG. 2 shows a cutaway view of the body 11 of the invention. In the present embodiment, the body is composed of two parts that are threadedly coupled: the chucking hold 17 and shroud 19. It is to be understood that chucking hold 17 and shroud 19 can be coupled by machine-fitted parts that are fused together by, for example, epoxy or heat activation. Thus, the threaded surface 37 can also be a smooth surface that is heat sealed or epoxied. Both form a body with an open interior and an exterior, the chucking hold and shroud being made from a thermally insulating material such as a thermal plastic, or a nylon-plastic (e.g., DELRIN™). The functional elements located within the body are as follows from the front end 101 of the body to the back end 103 of the body: the cooling tip 21, the cold sink 23, the thermoelectric module 25, the heat sink 27, and the gas tube 35. The cooling tip extends from the chucking hold 17 of the body at the front end 101, while the gas tube 35 extends from the shroud 19 of the body at the back end 103. Once in place, a space 43 is formed within the interior of the body that extends throughout the shroud to the back end 103. The space allows the heated gas to escape out the back 103 of the device The cooling tip, cold sink, thermoelectric module, and heat sink make thermal contact with one another and are held in place through pressure applied by compression spring 33 against the heat sink at spring inset 69. The thermoelectric module requires a DC power source, the voltage applied across wire leads 39 and 41, the wires exiting the power unit 13 and entering the back end 103 of the body to make contact with module 25. FIG. 4 shows the electrical wiring in greater detail. Also, gas tube 35 enters the back end 103 of the body, the terminal open end 29 having an opening smaller than the inside diameter of the tube to increase the pressure of the gas exiting the tube. The gas tube 35 is coupled to the power unit 13, the pressurized gas ultimately originating from an gas compressor. In another embodiment of the invention, a liquid carrying tube is used to provide a flow of cooling liquid such as water into and out of the apparatus.

Figure 3:
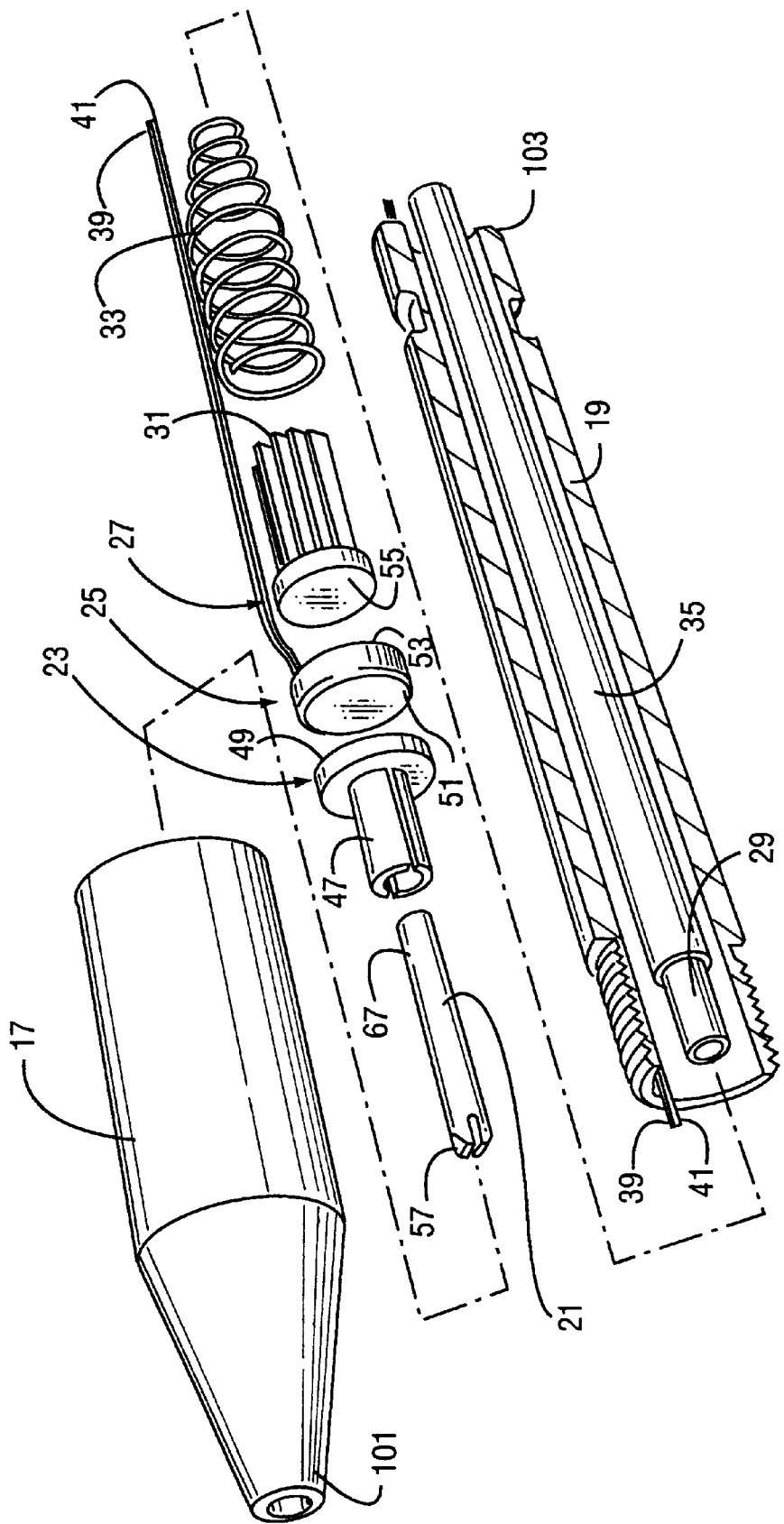
FIG. 3 is a perspective cutaway view of the components of the thermoelectric module, heat sink, and cooling sink of the invention.

FIG. 3 shows the coupling of the elements of the invention within the chucking hold 17 and shroud 19 in greater detail. The thermoelectric module 25 has a working face, or in the present embodiment, a cooling face 51, and a thermal sink face, or in the present embodiment, a heating face 53. All thermoelectric modules have a heating face and a cooling face. In the present embodiment of the invention, the cooling face is used to cool an external material or object. It is understood by those skilled in the art that the module could also be used to heat an external material or object.

A thermoelectric module, sometimes called a Peltier cooler, is a semiconductor-based electronic component that functions as a small heat pump. By applying a low DC voltage to the module, heat will be moved through the module from one side to the other. One module face, therefore, will be cooled while the opposing face is heated. The temperature range at which the module will perform is governed by the identity of the semiconductor and the efficiency of removing the heat generated at the heating face of the module. Thus, heat from the warmer area being cooled will pass from the cold face of the module to the heating face. To complete the thermal system, the heating face of the module must be attached to a heat suitable sink that is capable of dissipating both the heat pumped by the module and the heat created as a result of supplying electrical power to the module.

To accomplish the desired efficiency, the present invention incorporates a cold sink and a heat sink. The cooling face 51 makes thermal contact with the base end 49 of the cold sink 23. The cold sink 23 has a chuck end 47 for accepting the cooling tip 21. The chuck end 47 is designed such that the cooling tip can be easily replaced. Due to surface imperfections on faces 49, 51, 53, and 55, thermal contact is enhanced between the faces when a thermally conductive substance is applied to at least one of the surfaces. For example, commercially available thermal grease, epoxy, or other thermally conductive substance can be applied to at least one of the surfaces. Also, the surfaces can be soldered to obtain an improved thermal contact. At heating face 53 of the module the distal flat face 55 of the heat sink 27 makes thermal contact. Again, a thermal grease or epoxy can be applied to these faces to facilitate thermal contact.

In the embodiment of the invention in FIGS. 2 and 3, an air cooled heat sink is shown. Located on the air cooled heat sink 27 are a series of cooling fins 31 running parallel to one another and extend outward from the side opposite from and parallel to distal flat face 55. These fins act as a thermal sink for the heating face 53 of the thermoelectric module and allow the module create a larger temperature differential between the cold and hot faces, as well as increasing the life of the module.

The cooling tip 21 has a working end 57 and a proximal end 67, the proximal end being placed within the chuck end 47 of the cold sink. The cooling tip extends out the front end 101 of the body 11, and is held in place within the chucking hold by frictional contact within the chuck end 47. Since the cooling tip is frictionally held in place, the cooling tip can be easily replaced by pulling the tip from the chuck end. This facilitates hygienic use of the device, as well as versatility since the working end 57 can be formed in various shapes. The working end 57, shown in the embodiment in FIG. 3, is specially formed to receive a wire in the preferred embodiment of the invention. However, the working end 57 can be of various shapes and dimensions.

FIG. 4 shows a detailed description of the power unit 13 and its relationship to the body 11 of the invention. DC power supply 71 converts typical 120 volt AC voltage to a DC voltage, typically 2–5 volts. Gas pressure regulator 73 prevents the gas pressure coming from the gas compressor or other compressed gas source from exceeding 30 pounds of pressure as it exits tube 35 to enter the body 11. The on/off switch 77 extends outside the power unit 13 box, the switch being operatively coupled to the pneumatic pressure switch 75. This coupling is a safety means which prevents the DC power supply 71 from supplying current to body 11 through wires 39 and 41 unless there is adequate gas pressure in line 35. In the liquid cooled embodiment of the invention, a similar safety feature is provided. Line 83 supplies the compressed gas from an external source. Lead 81 carries the voltage from conventional 120 volt AC source.

As gas pressure reaches an adequate minimum level of 10 pounds, the DC current is activated to the thermoelectric module 25 and gas is provided simultaneously through gas tube 35. The open terminal end 29 is placed adjacent to the opposing fin 31 of the heat sink 27, as shown in FIG. 2. When positive gas pressure is applied to the system, gas flows across the fins. The cooling gas can be any non-corrosive, non-oxidizing and non-flammable gas such as nitrogen, air, or other inert gas. The relatively cool gas from the gas compressor draws heat away from the fins 29 and cools the heat sink 27, which in turn cools the heating face 53 of the thermoelectric module. The heated gas then passes out of the inside of the body 11 though space 43, and out the back end 103, as shown in FIG. 2.

Figures 5A, 5B, 5C:
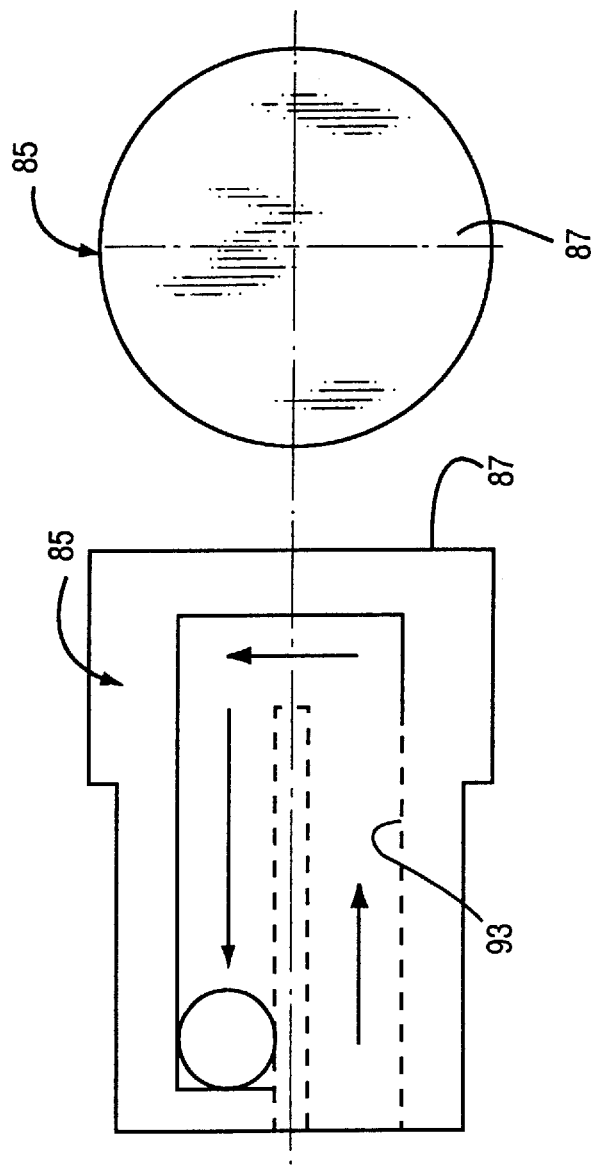
FIG. 5A is a isolated cutaway side view of the liquid cooled heat sink of the invention.
FIG. 5B is a top view of the liquid cooled heat sink.
FIG. 5C is a bottom view of the face contacting the thermoelectric module of the invention.

In another embodiment of the heat sink of the present invention a liquid such as water can be used to draw heat from the heat sink. Such a liquid cooled heat sink 85 is shown in one embodiment in FIG. 5. In the case of a liquid cooled device, tube 35 comprises two tubes coupled to an inlet 89 for cool liquid, channels 93 for the liquid to flow through the heat sink, and an outlet 91 for the heated liquid, the heated Liquid then being carried to an external radiator for cooling the liquid for recirculation. The liquid heat sink 85 would replace the fins of the gas cooled heat sink. The liquid cooled sink can be constructed by soldering thermally conductive tubing onto a flat plate of thermally conductive material, or by drilling holes in a metal block forming channels 93 through which, for example, water may pass as shown in the embodiment of the heat sink 85. Also, an elaborate serpentine water channel can be milled in a copper or aluminum block that later is sealed off with a cover plate, then placed against the heating face 53 of the module. In any case, surface 87 makes thermal contact with heating face 53 of the thermoelectric module, thus cooling the face to a high degree of efficiency.

Figure 6:
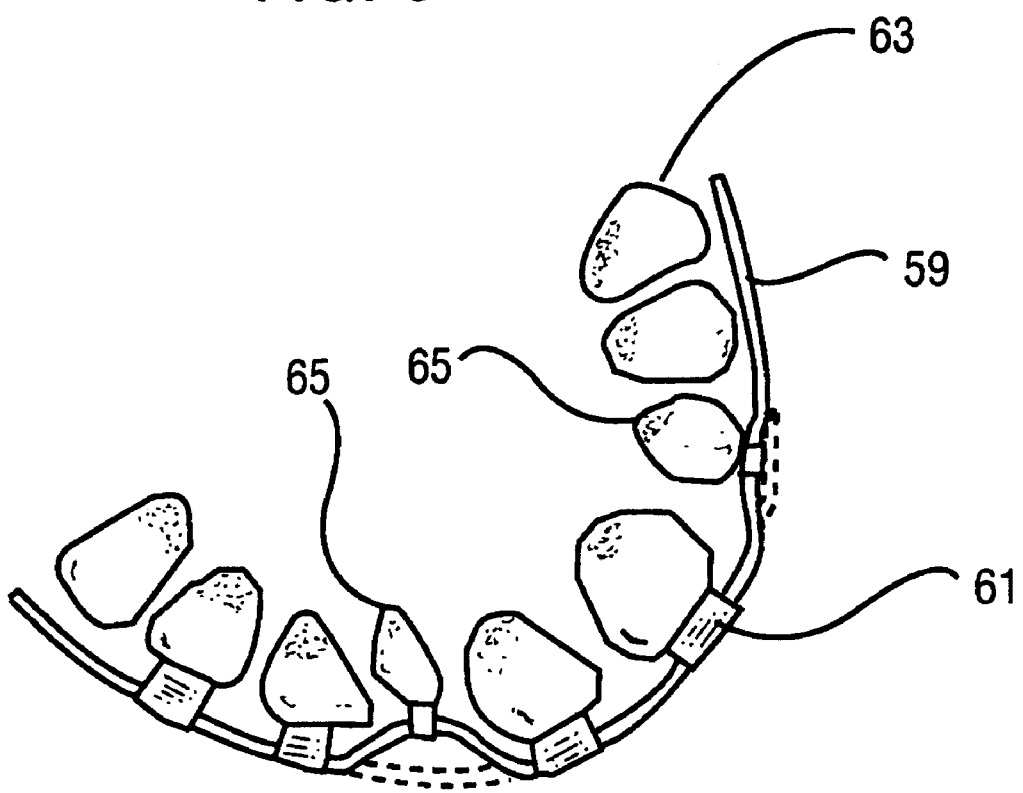
FIG. 6 is a top view of a row of human teeth demonstrating a shape memory allow archwire placement on the teeth.

DESCRIPTION OF METHOD. There are many dental, orthodontic, medical, and other uses for which the described embodiment of the present invention may be used. One preferred use is in orthodontic archwire attachment procedures. FIG. 6 shows a top view of an upper row of a patient's teeth with an archwire 59 attached to the normal teeth 63 through brackets 61. Archwire 59 is made of a shape memory alloy such as a NiTiCu alloy disclosed in Sachdeva et al. The alloy has two distinct physical states: the martensitic state and the austenitic state. The martensitic state is the supple soft state of the alloy that is achieved and maintained at a low temperature. The austenitic state is a stiffer and more rigid state of the alloy that is maintained at room or body temperature in the NiTiCu alloy.

In the austenitic state, the archwire is difficult to bend and form as is required in many orthodontic procedures. For example, as shown in FIG. 6, a maloccluded tooth 65 that is set back from the other teeth is difficult to reach by the small section of archwire without force to bend the wire from its initial rigid position as shown in dashed lines at maloccluded teeth 65. However, by cooling the dashed portion of the archwire, the wire is brought to its martensitic state, thus allowing easy forming into the bracket on teeth 65 and tooth 67. The dashed portion is cooled by engaging the cooling tip of the invention to that portion and forming the archwire to the desired shape. Once the cooling tip is removed, the patient's body heat will heat the archwire enough that it will tend to form to its natural shape as shown in dashed lines. Thus, the malocclusion can be corrected.

The cooling tip is applied to the archwire while both current and gas flow is provided to the body 11. The cooling tip can typically reach a temperature of about 2° C. The electric current creates the Peltier Cooling effect on the cooling face (and heating effect on the heating face) in the module, while the gas or liquid flow draws heat from the module. If heat is not withdrawn from the module, the cooling effect is limited since, due to basic thermodynamic principles, the module can cool only to the extent that heat is withdrawn from the module and removed from the system. Also, if heat is not withdrawn, due to the physical limitations of the semiconductor system, the module may overheat and malfunction. This could occur in a matter of 2–5 minutes. Thus, the design of the invention which incorporates the cooling fins 31 and the continuous gas or liquid flow through gas tube 35 provides a device which allows continuous use on the order of hours at a time.

The present invention offers several distinct advantages over the prior art. Current methods and devices used for forming shape memory archwire are cumbersome, being short lived and thus difficult to use for longer than a few moments. The present invention is an improvement over the prior art in that it allows continuous cooling of an archwire or other shape memory alloy for a continuous period of time for up to an hour or more.

Heat sink performance can be quantified by measuring the thermal resistance of the system, which is the difference between the heat sink temperature (degrees Celsius) and the ambient or coolant temperature divided by the heat input (watts) into the heat sink. The gas cooled or "forced convection" heat sink and gas tube configuration of the present invention can provide a thermal resistance value for the module of 0.02 to 0.5° C./watt. The liquid cooled heat sink can provide thermal resistance value of 0.01 to 0.1° C./watt. In a natural convection heat sink such as in the Tamler et al. invention the thermal resistance can be 0.5 to over 10° C./watt. As these figures show, there is a greater resistance in natural convection devices. Thus, better performance can be realized by the present invention over the prior art.

The present invention is simple and easy to use. The electronic circuitry is much simpler than the Tamler et al. device, thus, less expensive. The thermoelectric module temperature of the present invention is controlled by the design of the heat sink and the addition of the gas flow means. This allows for a stable cooling temperature to be maintained for longer periods of time.

The present invention allows for more versatility than the prior art. The cooling tip, which is the part of the apparatus that contacts the arch wire or other working area to be formed, can be changed easily so that the same device can be used on different patients without time consuming sterilization procedures. Further, the cooling tips can be of various designs to allow for a variety of uses.

While the invention has been shown in only one of its forms, it is not thus limited but is susceptible to various changes and modifications without departing from the spirit thereof.

what is claimed is:

1. A device for the continuous cooling of localized portions of a shape memory alloy, the device comprising:
   a body having an exterior and an initially open interior;
   a cooling tip extending from the open interior to the exterior of the body;
   a cold sink located within the body and coupled to the cooling tip;
   a thermoelectric module located within the body the module having a cooling face and a heating face, wherein the module is coupled to a DC power source;
   the cooling face of the thermoelectric module in thermal contact with the cold sink;
   a heat sink located within the body, the heating face of the thermoelectric module in thermal contact with the heat sink;
   a continuous flowing thermal removal means to absorb and remove excess heat at the heat sink; and
   an exhaust means for allowing the continuous flowing thermal removal means to exit the device, wherein a safety means is provided for breaking the electric power source to the thermoelectric module when no continuous flowing thermal removal means is flowing to the device.

2. The device in claim 1, wherein a pressurized gas flowing through a gas tube against the heat sink is the continuous flowing thermal removal means.

3. The device in claim 1, wherein a liquid flowing through the heat sink is the continuous flowing thermal removal means.

4. An orthodontic device for the continuous cooling of localized portions of a shape memory archwire, the device comprising:
   a body having an exterior and an initially open interior;
   a cold sink located within the body;
   a cooling tip extending from the open interior to the exterior of the body, the tip having a working end and a proximal end, the working end shaped for engaging an archwire and the proximal end thermally coupled to a cold sink;
   a thermoelectric module located within the body with a cooling face and a heating face, the module being powered by a DC voltage source;
   a cold sink located within the body, the cold sink having a base end for thermally contacting the cooling face of the thermoelectric module and a chuck end for holding the cooling tip;
   a heat sink located within the body, the heat sink having a distal flat face for making thermal contact with the heating face of the thermoelectric module and cooling fins for dissipating heat, wherein the heat sink is composed of a thermally conductive metal, the heat sink having a distal flat face and cooling fins, the distal flat face making thermal contact with the heating face of the thermoelectric module, and cooling fins to dissipate heat;
   a gas tube located within the body having an open terminal end, the gas tube being connected to a gas source for providing a flow of cooling gas through the device;
   the open terminal end of the tube being positioned adjacent the heat sink to allow pressurized gas to flow against the heat sink to absorb excess heat; and
   an exhaust means for allowing the heated gas to exit the device, wherein a safety means is provided for breaking the electric current to the thermoelectric module when no gas is flowing to the device.

5. The device in claim 4, wherein the thermoelectric module, cold and heat sinks, and cooling tip are housed within an insulating, hand held body.

6. The device in claim 5, further comprising a chuck end for frictionally holding the cooling tip.

7. The device in claim 4, wherein the means of providing cooling gas through the gas tube is a compressed gas source.

8. The device in claim 4, wherein the gas pressure supplied to the gas tube is regulated between 10 and 40 pounds of pressure.

9. The device in claim 4, further comprising a DC power unit to control electrical current to the thermoelectric module.

10. The device in claim 4, wherein the cooling tip is composed of a thermally conductive metal.

11. The device in claim 4, wherein the device creates a martensitic state in a shape memory alloy to thus allow forming a shape memory alloy wire to the desired shape.

12. A method of shaping a localized portion of a shape memory alloy archwire, the method comprising:
   providing a thermoelectric module powered by a DC power source, the module having a temperature differential, the module also having a working face and a thermal sink face;

transferring the thermal energy generated from the thermal sink face through a continuous flowing thermal removal means;

providing a means of thermal transfer from the working face of the thermoelectric module to a localized portion of a shape memory alloy, wherein a safety means is provided for breaking the electric current to the thermoelectric module when no gas is flowing to the device; and continuously contacting the shape memory alloy with the thermal transfer means in order to create a pliable state in the alloy and form the alloy into the desired shape.

13. The method of claim 12, wherein the continuous flowing thermal removal means is a pressurized gas.

14. The method of claim 12, wherein the continuous flowing thermal removal means is a liquid.

15. A method of shaping a localized portion of a shape memory alloy, the method comprising:

providing a cooling tip in thermal contact with a cold sink, the cooling tip having a working end that engages a shape memory allow archwire;

providing a thermoelectric module having a cooling face and a heating face, the heating face being in thermal contact with a heat sink and the cooling face being in thermal contact with a cold sink, wherein the heat sink is composed of a thermally conductive metal, the heat sink having a proximal flat face and cooling fins, the distal flat face making thermal contact with the heating face of the thermoelectric module, and cooling fins to dissipate heat;

forcing a stream of gas against the heat sink in order to regulate the temperature and allowing continuous use of the module; and applying the cooling tip to the desired portion of a shape memory alloy in order to form the alloy into the desired shape, wherein the working end of the cooling tip is indented in order to engage the shape memory alloy archwire.

16. The method of claim 15, wherein the thermoelectric module, cold and heat sinks, and cooling tip are housed within an insulating, hand held body.

17. The method of claim 15, wherein a means of providing pressurized gas is provided to force a stream of gas against the heat sink.

18. The method of claim 15, wherein the gas pressure supplied to the heat sink is regulated at between 10 and 40 pounds of pressure.

19. The method of claim 15, wherein a DC power unit is used to control electrical current to the thermoelectric cooling module.

20. The method of claim 19, wherein a means is provided for breaking the electric current to the thermoelectric module when no gas is flowing to the device.

21. The method of claim 15, wherein the cooling tip is composed of a thermally conductive metal.

22. The method of claim 15, wherein the device creates a martensitic state in a shape memory alloy to allow forming a shape memory alloy wire to the desired shape.

23. The method of claim 15, wherein the device maintains a constant cooling temperature at the cooling tip to allow continuous use for an extended period of time.

24. The method of claim 15, further providing a chucking end that frictionally holds the removable cooling tip in place.

* * * * *